United States Patent [19]

Ragains

[11] 4,112,766
[45] Sep. 12, 1978

[54] FLUID ACTUATED VALVE

[75] Inventor: Wilbur G. Ragains, Bartlesville, Okla.

[73] Assignee: Phillips Petroleum Company, Bartlesville, Okla.

[21] Appl. No.: 761,175

[22] Filed: Jan. 21, 1977

[51] Int. Cl.² .............................................. G01N 1/10
[52] U.S. Cl. .................................. 73/422 GC; 251/63; 285/137 R
[58] Field of Search ..................... 73/422 GC; 251/63; 285/137 R

[56] References Cited

U.S. PATENT DOCUMENTS

| | | | |
|---|---|---|---|
| 3,134,257 | 5/1964 | Reinecke | 73/27 |
| 3,140,615 | 7/1964 | Broerman | 73/422 |
| 3,223,123 | 12/1965 | Young | 73/422 GC |
| 3,376,894 | 4/1968 | Broerman | 137/625.48 |
| 3,387,496 | 6/1968 | Broerman | 73/422 |
| 3,535,939 | 10/1970 | Casey et al. | 73/427 GC |
| 3,545,491 | 12/1970 | Broerman | 137/625.48 |
| 3,827,449 | 8/1974 | Gurizzan et al. | 251/63 |

FOREIGN PATENT DOCUMENTS 679,606  1/1930  France ...................... 285/137

Primary Examiner—S. Clement Swisher

[57] ABSTRACT

A valve suitable for use with high pressure fluids comprises a valve housing formed as an integral body, a valve cap which is releasably secured to the valve housing, and an operating gas manifold body secured to the valve housing body. The operating gas lines can be secured to the manifold body by screw fittings and sealed to conically contoured passageways in the valve housing by correspondingly conically contoured ferrules. An end closure for the valve housing is held in place against spring bias by a split retention ring to provide a chamber for gas assist to an operating piston in high pressure applications.

15 Claims, 6 Drawing Figures

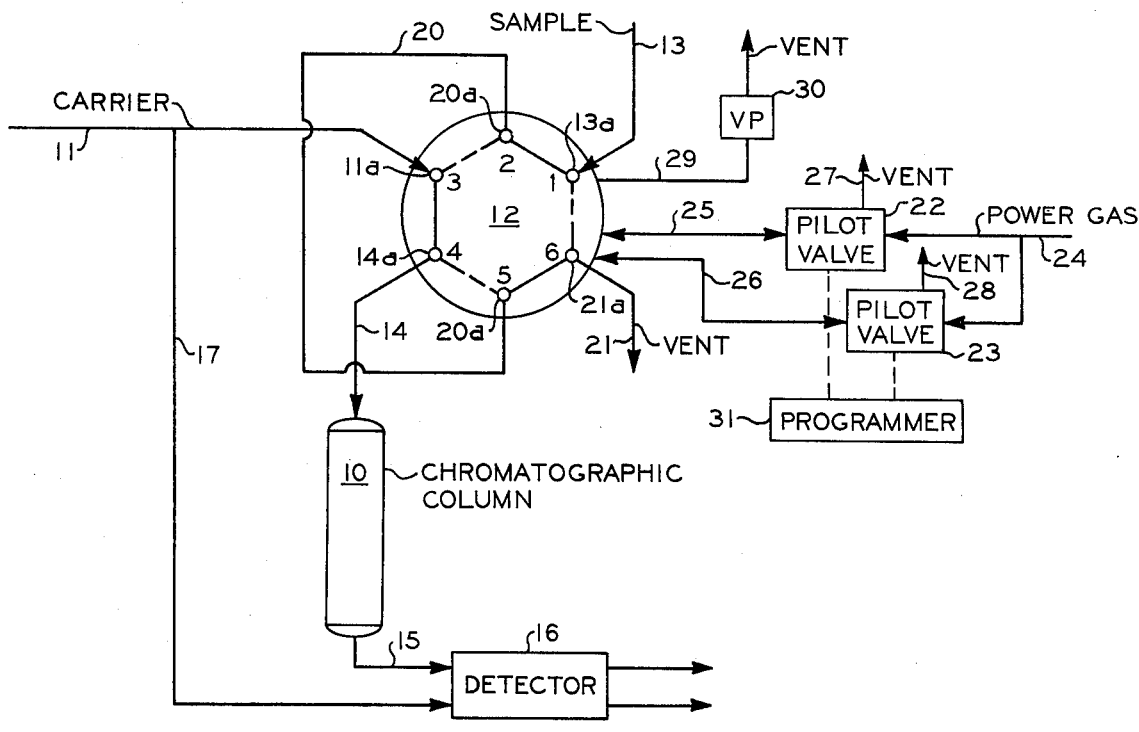
FIG. 1
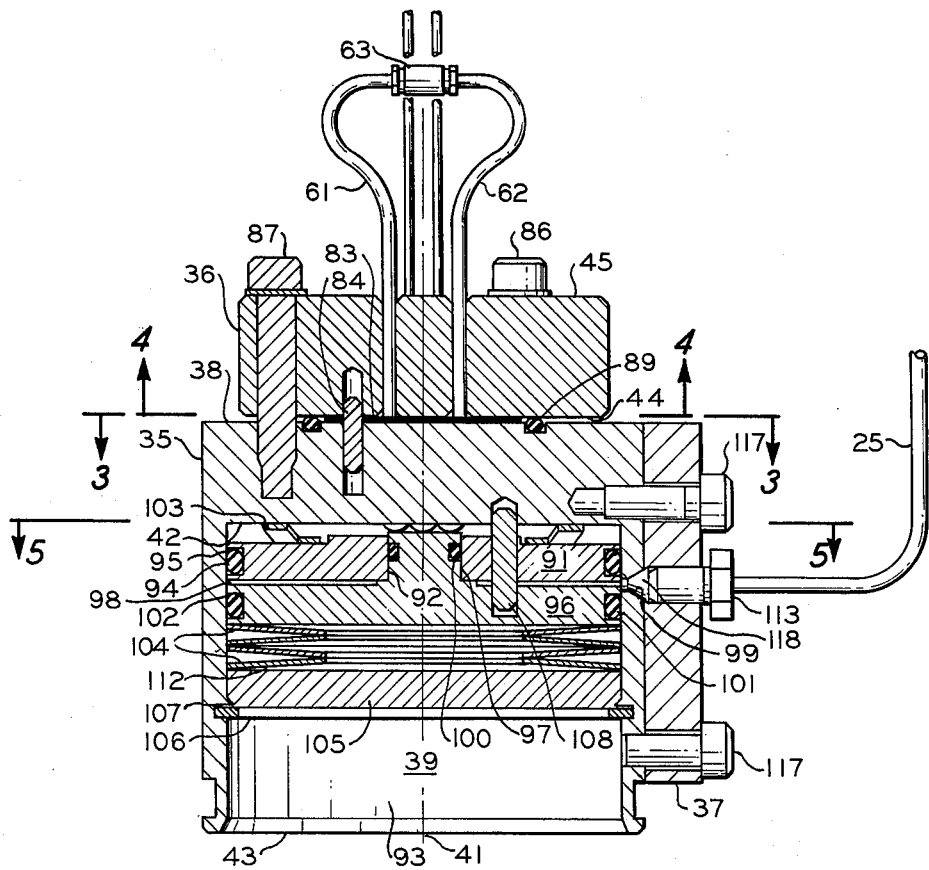

FLUID ACTUATED VALVE

This invention relates to a fluid actuated valve. In one aspect the invention relates to a gas actuated valve suitable for employment at high pressures in gas or liquid chromatography as a sample valve, a backflush valve or a column switching valve.

While there are numerous valves which have been found satisfactory for employment as sample valves or switching valves in low pressure gas chromatography, the advent of high pressure gas chromatography and liquid chromatography has created a need for improved valves which can function reliably and accurately at high fluid pressures, e.g. in the range of 200 to 6000 psi. Furthermore, with many previous valves, occurrences of leakage of actuating gas were not considered to present an unacceptable problem because plant instrument air was employed as the actuating gas and small losses of plant instrument air did not represent a significant cost. However, valves designed for use with high pressure gas samples and particularly with high pressure liquid chromatography samples generally require actuating gas at a higher pressure, e.g. 50 to 100 psi, than is available with plant instrument air. In such situations, high pressure bottled gas, such as air, helium, nitrogen, etc., can be employed, but any leakage can represent a significant cost. The employment of welded tubing connections to minimize leakage is disavantageous because welded tubing connections are readily broken off in handling. Similarly pressed fit connections are disadvantageous in any situation where the tubing may be subjected to rotation, as a rotation of even $\frac{1}{4}$ turn can result in substantial leakage.

Accordingly, it is an object of the present invention to provide a new and improved fluid actuated valve. Another object of the invention is to provide a valve which is reliable and accurate at high process fluid pressures. A further object of the invention is to reduce or eliminate the leakage of power gas in a gas actuated valve. Other objects, aspects and advantages of the invention will be apparent from a study of the specification, the drawings and the appended claims to the invention.

In the drawings,

FIG. 1 is a schematic representation of a chromatographic analyzer having the sample valve of this invention incorporated therein;

FIG. 2 is a view, in vertical cross section, of the sample valve employed in the analyzer of FIG. 1;

Figure 3:
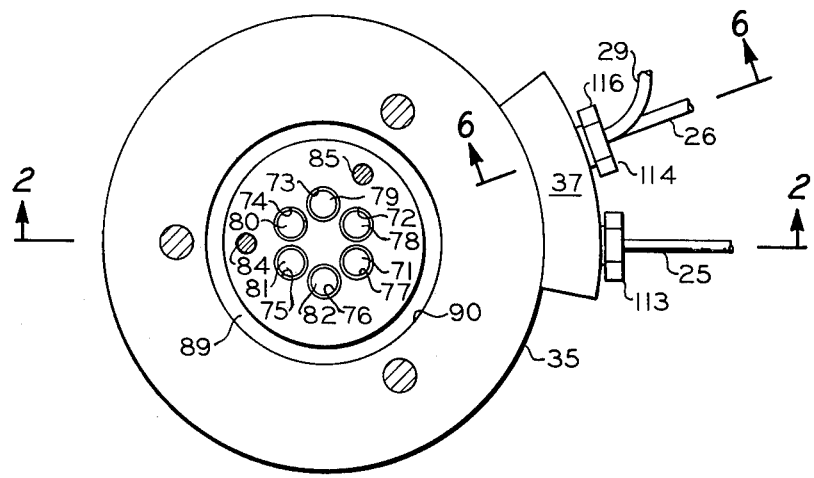
FIG. 3 is a view, in cross section, taken along line 3—3 in FIG. 2, illustrating the upper face of the valve housing.
Figure 6:
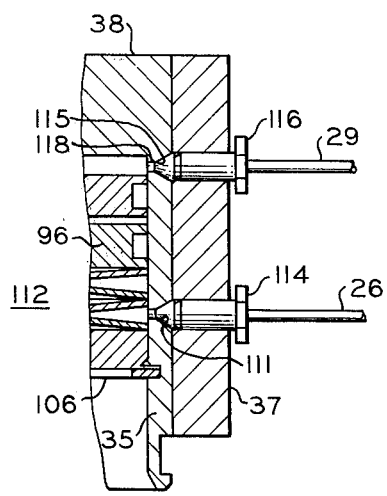
FIG. 6 is a partial view, in cross section, taken along line 6—6 in FIG. 3.

Referring now to the drawing in detail and to FIG. 1 in particular, there is shown a chromatographic column 10 which contains any suitable packing or partitioning material. Carrier fluid is introduced through a conduit 11 which communicates with a first inlet port 11a of the sample valve 12. This carrier fluid can either be a gas or a liquid, depending on the particular packing material and the desired separation. A sample fluid to be analyzed is introduced through a conduit 13 which communicates with an inlet port 13a of valve 12. A conduit 14 extends from a valve port 14a to the inlet of column 10. A conduit 15 extends from the outlet of column 10 to the first inlet of a detector 16. A portion of the carrier fluid is directed through a conduit 17 to a second inlet of detector 16. As is well known in the art, detector 16 can be any suitable instrument which is capable of providing an output signal that is representative of differences in composition of the two fluids passed thereto.

Sample valve 12 is employed to selectively introduce a slug of predetermined volume of sample to the inlet of column 10. This is accomplished by means of a sample loop 20 which extends between ports 20a and 20b. The volume of sample loop 20 is selected in accordance with the desired volume of sample to be introduced into the column 10. When the valve 12 is in the first position, the ports are connected in the directions shown by the solid lines. Carrier fluid thus flows from conduit 11 to conduit 14. Sample material flows from conduit 13 through sample loop 20 and is vented through a conduit 21 which communicates with a port 21a. When the sample valve 12 is actuated to the alternate position, the ports are connected in the direction shown by the illustrated broken lines. At this time, carrier fluid displaces the volume of sample trapped in sample loop 20 and forces this slug of sample into column 10. The incoming sample is passed to vent conduit 21 at this time. Sample valve 12 is pneumatically operated and receives operating pressure from pilot valves 22 and 23. Power gas is introduced into valves 22 and 23 through an inlet conduit 24. A conduit 25 extends between the pilot valve 22 and a first pneumatic port of sample valve 12. Similarly, a conduit 26 extends between the pilot valve 23 and a second pneumatic port of sample valve 12. Pilot valves 22 and 23 are provided with vent conduits 27 and 28, respectively. A conduit 29 extends from a third pneumatic port of sample valve 12 to a vacuum pump 30 to facilitate operation of the sample valve 12 under certain conditions, as described hereafter in greater detail. The operation of the sample valve 12 can be controlled by a programmer 31 which actuates pilot valves 22 and 23 at predetermined intervals.

The two-position, fluid actuated, diaphragm-sealed sample valve 12 is illustrated in greater detail in FIGS. 2, 3, 4, 5 and 6, and comprises a unitary housing body 35, a valve cap body 36, a manifold body 37, and the valve actuating components positioned within housing body 35. The unitary housing body 35 has a planar surface 38 at one end thereof and a cylindrical recess 39 formed in the opposite end thereof with the central axis 41 of the cylindrical recess 39 being perpendicular to the planar surface 38. The cylindrical recess 39 has a closed end 42 and an open end 43.

The valve cap body 36 has a planar first face 44 and an opposite face 45 and a plurality of spaced recesses 46, 47, 48, 49, 50 and 51 arranged in a suitable array in the planar first face 44 of the valve cap body 36. In the illustrated embodiment, the series of six recesses 46–51 are arranged in the form of spaced annular segments of a circular ring which is coaxial with cylindrical recess 39. The valve cap body 36 has a corresponding plurality of passageways, e.g. first, second, third, fourth, fifth and sixth spaced passageways 52, 53, 54, 55, 56 and 57, formed therein communicating between the spaced recesses 46, 48, 49, 51, 47 and 50, respectively, on the planar first face 44 of the valve cap body 36 and the opposite face 45 of the valve cap body. The lower ends of passageways 52, 53, 54, 55, 56 and 57 constitute the valve ports 13a, 20a, 11a, 14a, 20b and 21a, respectively. In the illustrated embodiment, valve 12 is connected to serve as a sample valve with an external sample loop 20 formed by the outer ends of conduits 61 and 62 being connected by tubing union 63 to provide fluid communication between recesses 47 and 50 of the desired sample volume. If desired, a groove of the desired volume can be formed in the planar face 44 of the valve cap body 36 extending from recess 47 to recess 50 to serve as an internal sample loop and passageways 56 and 57 can be plugged, or conduits 61 and 62 can be disconnected from each other and employed as separate flow conduits where valve 12 is being employed as a switching valve rather than as a sample valve.

The unitary housing body 35 has a number of linear passageways corresponding to the number of valved flow paths, e.g. first, second, third, fourth, fifth and sixth linear passageways 71, 72, 73, 74, 75 and 76 (FIG. 3), with each linear passageway extending perpendicularly from the planar surface 38 to the closed end 42 of the cylindrical recess 39. The cylindrical passageways 71–76 are positioned in an array corresponding to the array of recesses 46–51 such that each passageway 71–76 is in alignment with the space between a respective pair of the spaced recesses 46–51 and overlaps the adjuvant portions of the respective pair of recesses 46–51. Each passageway 71–76 is fitted with a plunger 77–82, respectively, which has a length greater than the length of the respective passageways 71–76 so as to extend into cylindrical recess 39. The plungers 77–82 can be metal rods as in Broerman, U.S. Pat. No. 3,387,496, or a series of spheres surmounted by a hemisphere having the flat surface thereof facing the valve cap body 36 as in Broerman, U.S. Pat. No. 3,376,894, or any other suitable plunger means.

Figure 4:
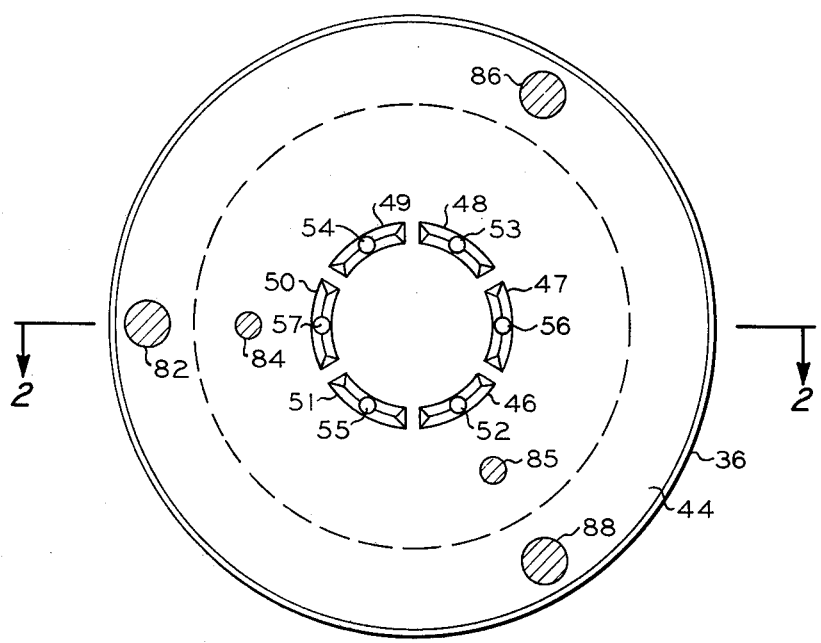
FIG. 4 is a view, in cross section, taken along the line 4—4 in FIG. 2, illustrating the lower face of the cap of the valve of FIG. 2.
Figure 5:
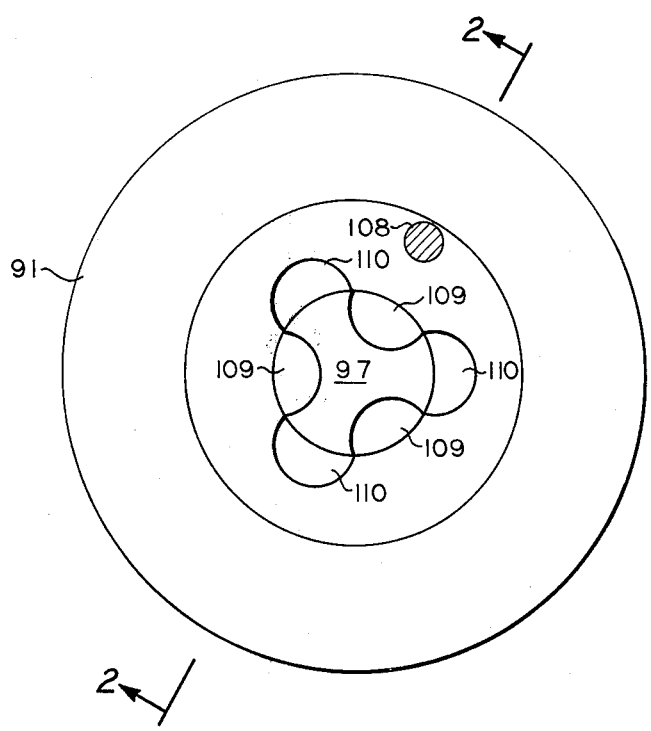
FIG. 5 is a partial view, in cross section, taken along line 5—5 in FIG. 2, illustrating the working faces of the pneumatic pistons in the valve of FIG. 2.

A diaphragm 83 is positioned against the planar first face 44 of the valve cap body 36 to encompass the portion of the planar first face 44 containing the spaced recesses 51–57, as shown by the dashed line in FIG. 4. Pins 84 and 85 can be secured in openings in either valve cap body 36 or housing body 35 with the other body having corresponding openings to provide for the mating of diaphragm 83, housing body 35 and valve cap body 36 only in a predetermined relationship. At least three cap screws 86, 87 and 88 can be employed to releasably secure the valve cap body 36 to the housing body 35 with the planar surface 38 of housing body 35 facing the planar first face 44 of valve cap body 36 with the diaphragm 83 positioned therebetween and the linear passageways 71–77 in alignment with the spaces between respective adjacent pairs of recesses 46–51. The use of cap screws 86, 87 and 88 to secure the valve cap body 36 to the housing body 35 permits the achievement of a greater sealing force between valve cap body 36 and housing body 35 than could be achieved by the use of other securing means such as a split retention ring in a cooperating groove in the inner wall of an annular housing body and a spring washer. The cap screws 86–88 are readily removed without the need for special tools. Thus, the use of the cap screws 86–88 permits the diaphragm to be cleaned or replaced without having to remove the valve from the chromatograph temperature controlled zone. An O-ring 89 can be positioned in annular groove 90 in face 38 coaxially with and spaced outwardly from the ring of recesses 46–51 to enhance the seal around the outer portion of diaphragm 83. The utilization of at least three cap screws avoids dishing distortion problems which can be encountered with a single cap screw or even with two cap screws. The diaphragm 83 has a diameter sufficiently large to completely cover the passageways 71–77 and the recesses 51–57, but it is desirable that the diameter of diaphragm 83 not be any larger than necessary to provide a desired safety margin, as the smaller the diameter the greater the sealing force per square inch between the diaphragm 83 and valve cap body 36 and valve housing body 35. The diaphragm 83 should be of a suitable flexible material, and can be a single layer of material or a plurality of layers of material. In one embodiment diaphragm 83 has three layers of material, the inner layer being formed of nylon and the two outer layers being formed of polytetrafluoroethylene.

An annular piston 91, having an axial opening 92 therethrough, is positioned in the cylindrical recess 39 for reciprocal movement along the central axis 41 of the cylindrical recess 39, in sealing engagement with the cylindrical wall 93 of the cylindrical recess 39. An O-ring 94 can be positioned in the annular groove 95 formed in the outer cylindrical wall of piston 91 to enhance the seal between piston 91 and housing body 35.

A second piston 96 is positioned in cylindrical recess 39 between annular piston 91 and the open end 43 for reciprocal movement along the central axis 41 of the cylindrical recess 39 in sealing engagement with the cylindrical wall 93 of the cylindrical recess 39. Piston 96 has a central projecting section 97 which extends upwardly from the main portion of piston 96 through the opening 92 in annular piston 91. The piston 96 and the annular piston 91 are of such configuration that a chamber 98 is formed between the main portion of piston 96 and annular piston 91. The annular wall of housing body 35 and manifold body 37 have a fluid passageway 99 extending therethrough in communication with chamber 98. One or more O-rings 100 can be employed to provide a seal between projecting section 97 and the cylindrical wall of opening 92. Piston 96 can be provided with an O-ring 101 positioned in the annular groove 102 in the cylindrical wall of piston 96 to provide a seal between piston 96 and housing body 35.

A spring 103 is positioned between the closed end 42 of cylindrical recess 39 and annular piston 91 to urge the annular piston 91 away from the closed end 42 of the cylindrical recess 39. A stack of Belleville spring washers 104 is positioned between a disc shaped closure member 105 and piston 96 to urge piston 96 toward the closed end 42 of the cylindrical recess 39. The closure member 105 is held in place by a split retention ring 106 positioned in annular groove 107 formed in the cylindrical wall 93 adjacent open end 43.

A pin 108 extends from a pit in the closed end 42 through an opening in piston 91 into an opening in piston 96 to provide and maintain the desired alignment of pistons 91 and 96 with the plungers 77–82. The lengths of the six plungers 77–82 and the configurations of annular piston 91 and piston 96 (the three spaced depressions 109 in the upper face of projecting section 97 of piston 96 and the three spaced depressions 110 in the upper face of piston 91 shown in FIG. 5) are such that only a first set of three of the six plungers 77–82 engages diaphragm 83 to seal the corresponding spaces between adjacent pairs of spaced recesses when the fluid pressure in chamber 98 is less than a first predetermined value and only the remaining set of three of the six plunger means engages said diaphragm to seal the corresponding spaces between adjacent pairs of spaced recesses when the fluid pressure in said chamber is greater than a second predetermined value which is higher than said first predetermined value. The actuating pistons 91 and 96 are biased in a manner that assures all six passages are momentarily closed during the switching operation, both energizing and de-energizing. This prevents unwanted mixing of streams during the switching cycle. The plungers 77–82 and the diaphram 83 move only a few thousandths of an inch to permit the flow between recesses. This small movement of plungers and diaphragm, along with the absence of sliding seals that contact the process fluid, eliminates the abrasions that can cause sample volume changes and valve leakage prevalent in slide type valves.

The unitary housing body 35 and manifold body 37 have a second fluid passageway 111 therethrough which communicates with a second chamber 112 constituted by the portion of cylindrical recess 39 between closure member 105 and piston 96. Conduit 26 is connected in fluid communication with passageway 111 by means of connector 114. Similarly conduit 25 is connected in fluid communication with passageway 99 by means of connector 113. The pilot valves 22 and 23 and programmer 31 constitute means for selectively applying fluid under pressure through conduit 25 and the first fluid passageway 99 to chamber 98 to move annular piston 91 toward closed end 42 of cylindrical recess 39 or through conduit 26 and the second fluid passageway 111 to the second chamber 112 to move piston 96 toward the closed end 42 of the cylindrical recess 39. The unitary housing body 35 and manifold body 37 have a third fluid passageway 115 therethrough which communicates with chamber 115, i.e., the space between piston 91 and the closed end 42 of the cylindrical recess 39. Conduit 29 is connected in fluid communication with passageway 115 by means of connector 116. The incorporation of closure member 105 and pneumatic conduit 26 permits the use of a gas pressure assist to the spring force applied to piston 96 by springs 104, thereby permitting the achievement of a greater port-to-port sealing force through the plungers 77–82 against diaphragm 83. Similarly the formation of valve housing body 35 as a single, integral unit permits the use of greater carrier fluid pressures and sample fluid pressures in recesses 46–51 without leakage than is generally achievable with the housing body formed in two separate pieces, e.g. as disclosed in U.S. Pat. No. 3,633,426.

In a presently preferred embodiment housing body 35 and valve cap body 36 are fabricated of stainless steel instead of aluminum to take advantage of the higher pressure rating achievable with steel. The utilization of split retention ring 106 to secure end closure 105 in valve housing body 35 permits the utilization of greater pneumatic pressures, minimizes distortion of the end closure and minimizes or eliminates any need for external clamps, as compared to the use of a single retention bolt as disclosed in U.S. Pat. No. 3,376,894. In general the split retention ring will also withstand a greater shearing force than a single bolt.

In the illustrated embodiment of the invention, resistance to leakage is substantially enhanced by the connections through manifold body 37. The manifold body 37 is preferably in the form of an annular segment, with the curvature of the inner cylindrical surface of manifold body 37 conforming to a portion of the cylindrically contoured external surface of valve housing body 35. Two cap screws 117 releasably secure manifold body 37 to valve housing body in the desired orientation. The outer portion of each of the passageways 99, 111 and 115 in the annular wall of valve housing body 35 has an outwardly diverging conical configuration adapted to receive the end of a piece of tubing having a correspondingly conically contoured annular ferrule 118 secured thereon. At least the outer portion of each of the passageways 99, 111 and 115 in the manifold body 37 is threaded to receive the respective male pipe fitting 113, 114 or 116. A seal is formed between each conically contoured annular ferrule 118 and the conically configured portion of the respective passageway. Thus it is not necessary to provide a seal between valve housing body 35 and manifold body 37. The manifold body 37 provides sufficient depth of material for the formation of the threaded portion of the passageways 99, 111 and 115 without the substantial increase in size and weight of valve housing body 35 which would otherwise be necessary in order to provide the threaded sections in the annular wall of the valve housing body 35. Such an increase in size would not only increase the cost of the valve, but would also make the valve more difficult to position in an analyzer assembly.

The valve of this invention is applicable in process chromatographic analyzers as a liquid or vapor sample valve, as a column switching valve and as a column backflush valve. It provides the uniform sample volume, the high reliability, the low internal volume and the fast switching speed required by process chromatography.

Reasonable variations and modifications are possible within the scope of the foregoing disclosure, the drawings and the appended claims to the invention.

That which is claimed is:

1. A two-position, fluid actuated, diaphragm-sealed valve, comprising in combination:

a unitary body having a planar surface at one end thereof and a cylindrical recess formed in the opposite end thereof with the central axis of said cylindrical recess being perpendicular to said planar surface, said cylindrical recess having a closed end and an open end;

a second body having a planar first face and an opposite face; said second body having a series of six spaced recesses arranged in a suitable array in said planar first face of said second body; said second body having first, second, third, and fourth spaced passageways formed therein communicating between a respective one of said spaced recesses on said planar first face of said second body and said opposite face of said second body; means adapted to provide fluid communication between the remaining two of said spaced recesses in said planar first face of said second body;

said unitary body having first, second, third, fourth, fifth and sixth linear passageways, with each said linear passageway extending perpendicularly from said planar surface to the closed end of said cylindrical recess;

a diaphragm positioned against said planar first face of said second body and encompassing the portion of said planar first face containing said spaced recesses;

means for releasably securing said second body to said unitary body with said planar surface facing said planar first face with said diaphragm positioned therebetween and with each said linear passageway being in alignment with the space between a respective pair of said spaced recesses;

six plunger means, with each plunger means being positioned in a respective one of said linear passageways;

closure means positioned adjacent the open end of said cylindrical recess to seal the open end of said cylindrical recess;

an annular piston means having an axial opening therethrough, said annular piston means being positioned in said cylindrical recess between said closure means and said closed end of said cylindrical recess for reciprocal movement along the central axis of said cylindrical recess in sealing engagement with the cylindrical wall of said cylindrical recess;

a second piston means positioned in said cylindrical recess between said closure means and said annular piston means for reciprocal movement along the central axis of said cylindrical recess in sealing engagement with the cylindrical wall of said cylindrical recess, said second piston means having an axially projecting section which extends from the main portion of said second piston means through said axial opening in said annular piston means, said second piston means and said annular piston means being of such configuration that a first chamber is formed between said main portion of said second piston means and said annular piston means, said unitary body having a first fluid passageway extending therethrough which communicates with said first chamber;

first spring means positioned between said closed end of said cylindrical recess and said annular piston means to urge said annular piston means away from said closed end of said cylindrical recess;

second spring means positioned between said closure member and said second piston means to urge said second piston means toward said closed end of said cylindrical recess;

the lengths of said six plunger means and the configurations of said annular piston means and said second piston means being such that only a first set of three of said six plunger means engages said diaphragm to seal the corresponding spaces between adjacent pairs of spaced recesses when the fluid pressure in said chamber is less than a first predetermined value and only the remaining set of three of said six plunger means engages said diaphragm to seal the corresponding spaces between adjacent pairs of spaced recesses when the fluid pressure in said chamber is greater than a second predetermined value which is higher than said first predetermined value;

said unitary body having a second fluid passageway therethrough which communicates with a second chamber constituted by the portion of said cylindrical recess between said closure member and said second piston means, means for selectively applying fluid under pressure through said first fluid passageway to said first chamber to move said annular piston means toward said closed end of said cylindrical recess or through said second fluid passageway to said second chamber to move said second piston means toward said closed end of said cylindrical recess.

2. A valve in accordance with claim 1 wherein said unitary body is provided with a cylindrically contoured external surface located between said planar surface and said open end, said first and second fluid passageways extending inwardly from said cylindrically contoured external surface, the outer portion of each of said first and second fluid passageways having an outwardly diverging conical configuration adapted to receive the end of a piece of tubing having a correspondingly conically contoured annular ferrule secured thereon; and further comprising an annular segment having an inner cylindrical surface corresponding to said cylindrically contoured external surface and third and fourth fluid passageways extending therethough at locations adapted to mate with said first and second fluid passageways, at least the outer portion of each of said third and fourth fluid passageways being threaded to receive a male pipe fitting, and means for securing said annular segment to said unitary body so that each of said third and fourth fluid passageways mates with a respective one of said first and second fluid passageways.

3. A valve in accordance with claim 2 wherein said means for securing said annular segment comprises means for releasably bolting said annular segment directly to said unitary body without providing a seal between said annular segment and said unitary body.

4. A valve in accordance with claim 3 wherein said closure means comprises a disc element, an annular groove in the cylindrical wall of said cylindrical recess, and a split retaining ring adapted to fit in said annular groove and hold said disc element against said second spring means.

5. A valve in accordance with claim 4 wherein said disc element has a cylindrical wall with an annular slot therein and an O-ring positioned in said annular slot to provide sealing contact with the cylindrical wall of said cylindrical recess.

6. A valve in accordance with claim 5 wherein said means for releasably securing said second body to said unitary body comprises at least three cap screws.

7. A valve in accordance with claim 6 wherein said unitary body and said second body are formed of stainless steel.

8. A valve in accordance with claim 1 wherein said closure means comprises a disc element, an annular groove in the cylindrical wall of said cylindrical recess, and a split retaining ring adapted to fit in said annular groove and hold said disc element against said second spring means.

9. A valve in accordance with claim 8 wherein said disc element has a cylindrical wall with an annular slot therein and an O-ring positioned in said annular slot to provide sealing contact with the cylindrical wall of said cylindrical recess.

10. A valve in accordance with claim 1 wherein said means for releasably securing said second body to said unitary body comprises at least three cap screws.

11. A two-position, fluid actuated, diaphragm-sealed valve, comprising in combination:

a valve housing body having a planar surface at one end thereof and a cylindrical recess formed in the opposite end thereof with the central axis of said cylindrical recess being perpendicular to said planar surface, said cylindrical recess having a closed end and an open end;

a second body having a planar first face and an opposite face; said second body having a plurality of spaced recesses arranged in a suitable array in said planar first face of said second body; said second body having a plurality of spaced passageways formed therein communicating between a respective one of said spaced recesses on said planar first face of said second body and said opposite face of said second body;

said valve housing body having a plurality of linear passageways, with each said linear passageway extending perpendicularly from said planar surface to the closed end of said cylindrical recess;

a diaphragm positioned against said planar first face of said second body and encompassing the portion of said planar first face containing said spaced recesses;

means for releasably securing said second body to said valve housing body with said planar surface facing said planar first face with said diaphragm positioned therebetween and with each said linear passageway being in alignment with the space between a respective pair of said spaced recesses;

a plurality of plunger means, with each plunger means being positioned in a respective one of said linear passageways;

closure means positioned adjacent the open end of said cylindrical recess to seal the open end of said cylindrical recess;

an annular piston means having an axial opening therethrough, said annular piston means being positioned in said cylindrical recess between said closure means and said closed end of said cylindrical recess for reciprocal movement along the central axis of said cylindrical recess in sealing engagement with the cylindrical wall of said cylindrical recess;

a second piston means positioned in said cylindrical recess between said closure means and said annular piston means for reciprocal movement along the central axis of said cylindrical recess in sealing engagement with the cylindrical wall of said cylindrical recess, said second piston means having an axially projecting section which extends from the main portion of said second piston means through said axial opening in said annular piston means, said second piston means and said annular piston means being of such configuration that a first chamber is formed between said main portion of said second piston means and said annular piston means, said valve housing body having a first fluid passageway extending therethrough which communicates with said first chamber;

first spring means positioned between said closed end of said cylindrical recess and said annular piston means to urge said annular piston means away from said closed end of said cylindrical recess;

second spring means positioned between said closure member and said second piston means to urge said second piston means towards said closed end of said cylindrical recess;

the lengths of said plunger means and the configurations of said annular piston means and said second piston means being such that only a first set of said plunger means engages said diaphragm to seal the corresponding spaces between adjacent pairs of spaced recesses when the fluid pressure in said chamber is less than a first predetermined value and only the remaining set of said plunger means engages said diaphragm to seal the corresponding spaces between adjacent pairs of spaced recesses when the fluid pressure in said chamber is greater than a second predetermined value which is higher than said first predetermined value;

said valve housing body having a second fluid passageway therethrough which communicates with a second chamber constituted by the portion of said cylindrical recess between said closure member and said second piston means, means for selectively applying fluid under pressure through said first fluid passageway to said first chamber to move said annular piston means toward said closed end of said cylindrical recess or through said second fluid passageway to said second chamber to move said second piston means toward said closed end of said cylindrical recess;

said valve housing body being provided with a contoured external surface located between said planar surface and said open end, said first and second fluid passageways extending inwardly from said contoured external surface, the outer portion of each of said first and second fluid passageways having an outwardly diverging conical configuration adapted to receive the end of a piece of tubing having a correspondingly conically contoured annular ferrule secured thereon; and an annular segment having an inner surface corresponding to said contoured external surface, third and fourth fluid passageways extending through said annular segment at locations adapted to mate with said first and second fluid passageways, at least the outer portion of each of said third and fourth fluid passageways being threaded to receive a male pipe fitting, and means for securing said annular segment to said valve housing body so that each of said third and fourth fluid passageways mates with a respective one of said first and second fluid passageways.

12. A valve in accordance with claim 11 wherein said means for securing said annular segment comprises means for releasably bolting said annular segment directly to said unitary body without providing a seal between said annular segment and said unitary body.

13. A two-position, fluid actuated, diaphragm-sealed valve, comprising in combination:

a unitary body having a planar surface at one end thereof and a cylindrical recess formed in the opposite end thereof with the central axis of said cylindrical recess being perpendicular to said planar surface, said cylindrical recess having a closed end and an open end;

a second body having a planar first face and an opposite face; said second body having a plurality of six spaced recesses arranged in a suitable array in said planar first face of said second body; said second body having a plurality of spaced passageways formed therein communicating between a respective one of said spaced recesses on said planar first face of said second body and said opposite face of said second body;

said unitary body having a plurality of linear passageways, with each said linear passageway extending perpendicularly from said planar surface to the closed end of said cylindrical recess;

a diaphragm positioned against said planar first face of said second body and encompassing the portion of said planar first face containing said spaced recesses;

means for releasably securing said second body to said unitary body with said planar surface facing said planar first face with said diaphragm positioned therebetween and with each said linear passageway being in alignment with the space between a respective pair of said spaced recesses;

a plurality of plunger means, with each plunger means being positioned in a respective one of said linear passageways;

closure means positioned adjacent the open end of said cylindrical recess to seal the open end of said cylindrical recess;

an annular piston means having an axial opening therethrough, said annular piston means being positioned in said cylindrical recess between said closure means and said closed end of said cylindrical recess for reciprocal movement along the central axis of said cylindrical recess in sealing engagement with the cylindrical wall of said cylindrical recess;

a second piston means positioned in said cylindrical recess between said closure means and said annular piston means for reciprocal movement along the central axis of said cylindrical recess in sealing engagement with the cylindrical wall of said cylindrical recess, said second piston means having a projecting section which extends from the main portion of said second piston means through said axial opening in said annular piston means, said second piston means and said annular piston means being of such configuration that a first chamber is formed between said main portion of said second piston means and said annular piston means, said unitary body having a first fluid passageway therethrough which communicates with said first chamber;

first spring means positioned between said closed end of said cylindrical recess and said annular piston means to urge said annular piston means away from said closed end of said cylindrical recess;

second spring means positioned between said closure member and said second piston means to urge said second piston means toward said closed end of said cylindrical recess;

the lengths of said plunger means and the configurations of said annular piston means and said second piston means being such that only a first set of said plunger means engages said diaphragm to seal the corresponding spaces between adjacent pairs of spaced recesses when the fluid pressure in said chamber is less than a first predetermined value and only the remaining set of said plunger means engages said diaphragm to seal the corresponding spaces between adjacent pairs of spaced recesses when the fluid pressure in said chamber is greater than a second predetermined value which is higher than said first predetermined value;

said unitary body having a second fluid passageway therethrough which communicates with a second chamber constituted by the portion of said cylindrical recess between said closure member and said second piston means, means for selectively applying fluid under pressure through said first fluid passageway to said first chamber to move said annular piston means toward said closed end of said cylindrical recess or through said second fluid passageway to said second chamber to move said second piston means toward said closed end of said cylindrical recess.

14. A valve in accordance with claim 13 wherein said unitary body is provided with a cylindrically contoured external surface located between said planar surface and said open end, said first and second fluid passageways extending inwardly from said cylindrically contoured external surface, the outer portion of each of said first and second fluid passageways having an outwardly diverging conical configuration; and further comprising an annular segment having an inner cylindrical surface corresponding to said cylindrically contoured external surface and third and fourth fluid passageways extending therethrough at locations adapted to mate with said first and second fluid passageways, at least the outer portion of each of said third and fourth fluid passageways being threaded to receive a male pipe fitting, and means for securing said annular segment to said unitary body so that each of said third and fourth fluid passageways mates with a respective one of said first and second fluid passageways, first and second tubing means with each tubing means extending through a respective one of said third and fourth fluid passageways and having a correspondingly conically contoured annular ferrule secured thereon positioned in the outwardly diverging conically configured portion of the respective one of said first and second fluid passageways; first and second male pipe fittings with each fitting being positioned about a respective one of said first and second tubing means and secured to the threaded portion of the respective one of said third and fourth fluid passageways.

15. A valve in accordance with claim 14 wherein said means for securing said annular segment comprises means for releasably bolting said annular segment directly to said unitary body without providing a seal between said annular segment and said unitary body.

* * * * *